US006291693B1

(12) United States Patent
Holick et al.

(10) Patent No.: US 6,291,693 B1
(45) Date of Patent: Sep. 18, 2001

(54) KITS COMPRISING LABELED VITAMIN D COMPOUNDS

(75) Inventors: Michael F. Holick, Sudbury; Rahul Ray, Wayland, both of MA (US)

(73) Assignee: A & D BioScience, Inc., Sudbury, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/345,789

(22) Filed: Jul. 1, 1999

Related U.S. Application Data

(63) Continuation of application No. 09/091,184, filed on Jun. 10, 1998, now Pat. No. 5,981,779, and a continuation of application No. PCT/US96/20341, filed on Dec. 24, 1996.
(60) Provisional application No. 60/009,432, filed on Dec. 29, 1995.

(51) Int. Cl.$^7$ .................................................. C07C 401/00
(52) U.S. Cl. .......................................... 552/653; 435/975
(58) Field of Search .............................. 552/653; 435/975

(56) References Cited

U.S. PATENT DOCUMENTS

| | | | |
|---|---|---|---|
| 4,297,289 | 10/1981 | DeLuca et al. | 260/397.2 |
| 4,585,741 | 4/1986 | Clevinger et al. | 436/542 |
| 4,604,364 | 8/1986 | Kosak | 436/501 |
| 4,816,417 | 3/1989 | DeLuca et al. | 436/501 |
| 4,857,652 | 8/1989 | Schaap | 549/510 |
| 4,931,569 | 6/1990 | Edwards et al. | 549/221 |
| 4,933,276 | 6/1990 | Baret | 435/7 |
| 4,959,182 | 9/1990 | Schaap | 252/700 |
| 4,962,192 | 10/1990 | Schaap | 536/18.1 |
| 5,004,565 | 4/1991 | Schaap | 252/700 |
| 5,232,836 | 8/1993 | Bouillon et al. | 435/8 |
| 5,248,618 | 9/1993 | Haces | 436/172 |
| 5,411,949 | 5/1995 | Neef et al. | 514/167 |
| 5,428,029 | 6/1995 | Doran et al. | 514/167 |
| 5,430,196 | 7/1995 | DeLuca et al. | 568/665 |
| 5,981,779 | * 11/1999 | Holick et al. | 552/653 |

FOREIGN PATENT DOCUMENTS

| | | |
|---|---|---|
| 0 363 211 A1 | 4/1990 | (EP). |
| 6-41058 | 2/1994 | (JP). |

OTHER PUBLICATIONS

Barsony, J. et al., "Development of a Biologically Active Fluorescent–Labeled Calcitriol and Its Use to Study Hormone Binding to the Vitamin D Receptor," *Anal. Biochem.* 229: 68–79 (1995).

STN File Caplus, Accession No. 1992:84004, abstract of Tanabe, M. et al., "Synthesis and assignment of novel iodine–125–labeld 1a, 25–dihydroxyvitamin D3 derivatives," *J. Nutr. Sci. Vitaminol.* 37:139–147 (1991).

European Search Report for Eurpoean Application No. EP 96 94 4506, mailed Mar. 3, 2000.

Chen, T.C. et al., "Methods for the determination of the circulating concentration of 25–hydroxyvitamin D," *J. Nutr. Biochem.* 1:315–319 (Jun. 1990).

Chen, T.C. et al., "A method for the determination of the circulating concentration of vitamin D," *J. Nutr. Biochem.* 1:272–276 (May 1990).

Chen, T.C., et al., "A method for the determination of the circulating concentration of 1,25–dihydroxyvitamin D," *J. Nutr. Biochem.* 1:320–327 (Jun. 1990).

Engvall, E., "Enzymes Immunoassay ELISA and EMIT," in *Methods in Enzymology*, vol. 70, Academic Press, New York, pp. 419–439 (1980).

Holick, M.F., "Vitamin D: Biosynthesis, Metabolism, and Mode of Action," in *Endocrinology* 2$^{nd}$ Edition, vol. 2, DeGroot, L.J., et al., eds., Saunders, W.B., Philadelphia, pp. 902–926 (1989).

Holick, M.F., et al., "The Vitamin D Content of Fortified Milk and Infant Formula," *New England J. Med.* 326:1178–1181 (Apr. 1992).

Holick, M.F., et al., "Calcium, Phosphorus, and Bone Metabolism: Calcium–Regulating Hormones," in *Harrison's Principles of Internal Medicine*, 13$^{th}$ Edition, vol. 2, Isselbacher, K.J., et al., eds., McGraw–Hill, Inc., New York, pp. 2137–2151 (1994).

Ray, R., et al., "Evaluation of a Photolabile Derivative of 1,25–Dihydroxyvitamin $D_3$ as a Photoaffinity Probe for 1,25–Dihydroxyvitamin–$D_3$ Receptor in Chick Intestinal Cytosol," *Biochem. Biophys. Res. Comm.* 132:198–203 (1985).

Ray, R., et al., "Photoaffinity Labeling of the Rat Plasma Vitamin D Binding Protein with [26,27,–$^3$H]–25–Hydroxyvitamin $D_3$ 3β–[N–(4–Azido–2–nitrophenyl)glycinate]," *Biochem.* 25:4729–4733 (1986).

Ray, R., et al., "Photoaffinity Labeling of Human Serum Vitamin D Binding Protein and Chemical Cleavages of the Labeled Protein: Identification of an 11.5–kDa Peptide Containing the Putative 25–Hydroxyvitamin $D_3$ Binding Site," *Biochem.* 30:7638–7642 (1991).

Shimizu, M., et al., "Synthesis of a reagent for fluorescence–labeling of vitamin D and its use in assaying vitamin D metabolites," CAPLUS, American Chemical Society, CA 115:962, abstract of *Anal. Biochem.* 194:77–81 (1991).

Shimzu, M., et al., "Fluorescent–labeling reaction of vitamin D metabolites and analogs with fluorescent 1,2,4–triazoline–3,5–dione (DMEQ–TAD)," CAPLUS, American Chemical Society, CA 121:83738, abstract of *Bioorg. Med. Chem. Lett.* 3:1809–1814 (1993).

(List continued on next page.)

Primary Examiner—Ralph Gitomer
(74) Attorney, Agent, or Firm—Sterne, Kessler, Goldstein & Fox P.L.L.C.

(57) ABSTRACT

Kit comprising biotin, fluorescent and chemiluminescent labeled vitamin D compounds are disclosed. The disclosed kit may be used in assays for the presence of vitamin D, its metabolites and vitamin D analogs in biological fluids.

17 Claims, 6 Drawing Sheets

OTHER PUBLICATIONS

Tanabe, M., et al., "Preparation of vitamin D derivatives containing a substituent at the 25–hydroxy group," CAPLUS, American Chemical Society, CA 121:109401, abstract of JP 06041058 (1994).

Tanner, J.T., et al., "Survey of Vitamin Content of Fortified Milk," *J. Assoc. Off. Anal. Chem.* 71:607–610 (May 1988).

English language abstract for JP 6–41058 (Document AM1), Derwent World Patents Index.

Tanabe, M. et al., "Synthesis and Assignment of Novel [$^{125}$I]–Labeled 1α,25–Dihydroxyvitamin $D_3$ Derivatives," *J. Nutr. Sci. Vitaminol.* 37:139–147, University of Tokyo Press (1991).

English language abstract for JP 6–41058 (Document No. AM1), Patent Abstracts of Japan (JAPIO).

\* cited by examiner

KITS COMPRISING LABELED VITAMIN D COMPOUNDS

This is a continuation of U.S. application Ser. No. 09/091,184, filed Jun. 10, 1998, now U.S. Pat. No. 5,981,779, and a continuation of PCT/US96/20341, filed Dec. 27, 1996 and claims the benefit of provisional application 60/009,432, filed Dec. 29, 1995.

BACKGROUND OF THE INVENTION

1. Field of the Invention

The present invention relates to non-radioactive vitamin D compounds and methods to assay for the presence of vitamin D, vitamin D analogs and their metabolites which may be present in milk, blood or other biological fluids. The assay methods employed in this invention may be enzyme linked immunoassays (ELISAs) (with biotin containing compounds) and fluorimetric and chemiluminometric assays (with fluorescein or chemiluminiscence containing compounds).

2. Related Art

It is well-established that cutaneously synthesized vitamin $D_3$, a seco-steroid, undergoes sequential metabolic conversions to 25-hydroxyvitamin $D_3$ (25-OH-$D_3$) in the liver and to 1,25(OH)$_2$$D_3$ in the kidney. 1,25(OH)$_2$$D_3$, the dihydroxylated metabolite of vitamin $D_3$, is the most active form of vitamin D hormone which is intimately involved in calcium and phosphorous homeostasis (Holick, M. F. (1989), "Vitamin D: biosynthesis, metabolism and mode of action." In *Endocrinology*, vol. 2, Degroot et al. (eds.), Saunders, W. B., Philadelphia, pp. 902–926). In addition to vitamin $D_3$ (synthesized in the skin), another chemical form of vitamin $D_3$, called vitamin $D_2$, exists in nature. Vitamin $D_2$ is metabolized to 25-hydroxyvitamin $D_2$ (25-(OH)$_2$-D) and 1,25(OH)$_2$$D_2$ in a manner similar to vitamin $D_3$. Vitamin $D_2$ is obtained primarily from diet and vitamin D supplementation, and can be as little as 5–10%, or as high as 100% of the circulating concentration of 25-OH-D depending on the relative amounts of vitamin $D_2$ present in the diet and cutaneously-produced vitamin $D_3$ by exposure to sunlight (Holick, M. F. et al. (1986) "Calcium, phosphorus and bone metabolism: calcium regulating hormones," in *Harrison's Principles of Internal Medicine*, 13th Ed., Braunwald et al. (eds.), McGraw-Hill, New York, pp. 2137–2151). In the following discussion, it may be assumed that vitamin D, 25-OH-D and 1,25(OH)$_2$D will represent the total pool of vitamin D and its metabolites, unless otherwise mentioned.

Biosynthesis of 25-OH-D and 1,25(OH)$_2$D and their metabolism are regulated by the factors that control mineral and skeletal metabolism (Holick, M. F. (1989)). As a result, the serum 1,25(OH)$_2$D level is an important pathophysiological indicator in several diseases. For example, production of 1,25(OH)$_2$D is strongly influenced by a number of diseases such as acquired or inherited disorders of vitamin D-metabolism, including renal osteodystrophy, certain metabolic bone diseases, sarcoidosis, hypercalcemia associated with chronic granulotomous disorders, and vitamin D-dependent rickets types I and II (Holick, M. F. et al. (1986)).

On the other hand, the circulating concentration of 25-OH-D is considered to be an important indicator of vitamin D status in man (Holick, M. F. (1989); Holick, M. F. et al. (1986)). For example, hypovitaminosis, which results from the insufficient endogenous production of vitamin D in the skin, and insufficient dietary supplementation, and/or inability of the small intestine to absorb adequate amounts of vitamin D from diet, results in hypocalcemia and hypophosphatemia and corresponding secondary hyperparathyroidism (Holick, M. F. et al. (1986)). Vitamin D-deficiency is best determined in a clinical setting by measuring 25-OH-D in blood. When the 25-OH-D concentration is below the low limit of the normal range, the patient is considered to be deficient in vitamin D. Hypovitaminosis D also results in disturbances in mineral metabolism (i.e., rickets and osteomalacia in children and adults, respectively).

Serum 25-OH-D-levels are also found to be lower than normal in intestinal malabsorption syndromes, liver disorders (chronic and acute), and nephrotic syndromes. In osteopenia in the aged, serum 25-OH-D levels are often found to be lower than normal. In cases of vitamin D intoxication, serum 25-OH-D level is found, as expected, to be higher than normal (Holick, M. F. et al. (1986)).

Considerable efforts have been directed towards developing assays for accurately measuring concentrations of 25-OH-D in circulation, given its pathophysiological importance. The 25-OH-D assays have been developed for measuring vitamin D status, especially in the elderly and patients with liver diseases and intestinal disorders.

The most efficient methods for assaying 25-OH-D known to date include different variations of a theme that involves competitive binding between 'cold' and 'hot' (radioactive) 25-OH-$D_3$ with normal or vitamin D-deficient rat serum (rat DBP). A standard curve is set up with measured quantities of 25-OH-$D_3$. An organic extract of a blood sample is added to the assay, and concentration of 25-OH-D is determined from the standard curve. Serum-concentration of 25-OH-D is much higher (on the order of 100–1000-fold) than the dihydroxylated metabolites of vitamin D, and hence these metabolites do not interfere with the assay in any significant way. This situation is further aided by higher binding avidity of DBP towards 25-OH-D compared with other dihydroxylated metabolites of vitamin D. Furthermore, DBP does not discriminate between 25-OH-$D_2$ and 25-OH-$D_3$, and hence the measured concentration of 25-OH-D in serum represents the total concentration of 25-OH-$D_2$ and 25-OH-$D_3$ (Chen et al., *J. Nutritional Biochem.* 1:315–319 (1990)).

DeLuca, U.S. Pat. No. 4,297,289, discloses vitamin D compounds isotopically labeled at the 6-position with deuterium or tritium atoms and the use thereof in vitamin D metabolite analyses.

DeLuca, U.S. Pat. No. 4,816,417, discloses a competitive binding assay for the presence of 1,25(OH)$_2$$D_x$, where x is 2, 3, 4, 5 and/or 6, in a sample containing vitamin D transport protein. According to this assay, receptor protein which is capable of binding to 1,25(OH)$_2$D and labeled 1,25(OH)$_2$D is added to the sample together with an antibody capable of binding to the receptor protein. One then measures the relative degree of binding of labeled 1,25-(OH)$_2$D to the receptor protein. The 1,25(OH)$_2$D is radiolabeled.

The above-mentioned assays, despite their specificity and efficiency, suffer from a few drawbacks. These assays are time-consuming and costly. The most important problem is, however, the intrinsic use of radioactivity. Radioisotopes are very costly, hazardous to handle and store. Radioactive disposal is also becoming an extremely costly affair.

An HPLC-UV detection method, which largely does not use radioactivity, has also been developed for assaying 25-OH-D (Jones, G., *Clin. Chem.* 24:287–298 (1978)). This method involves multiple chromatographic separations, and final detection and measurement of peaks corresponding to 25-OH-D$_2$ and 25-OH-D$_3$. Although this method provides one of the most accurate measurement of 25-OH-D in serum, it suffers from two major drawbacks. For example, measurement of 25-OH-D is limited by the detection limit of the UV detector. Therefore, 2 ml of blood is needed for the assay. This volume requirement is a particularly difficult problem for determining 25-OH-D levels in younger children. In addition, the assay procedure is very labor intensive and, therefore, very costly.

A non-radioactive method involving isotope-dilution mass spectrometry has also been developed. In this method, a serum sample is spiked with a synthetic analog of 25-OH-D$_3$ which is labeled with stable H-atoms (i.e., deuterium at C-26(27) (Bjorkhem and Holmberg, *Clin. Chim. Acta* 68:215–224 (1976)) or C6 and C-19 positions (Ray, R. et al., *Steroids* 57:142–146 (1992)). The 'spiked' serum samples are processed in the usual fashion, i.e. extraction and partial purification of 25-OH-D fraction (by various chromatographic steps), and subjected to mass spectrometry. Concentration of metabolite in the serum is determined by the relative abundance of a particular "molecular fragment" (generated from the parent metabolite) compared with that of the labeled fragment. This method, although very accurate, has received little practical application due to the requirement of highly sophisticated and expensive instrumentation. This method is also very time-consuming and costly. Furthermore, this method is specific for either 25-OH-D$_3$ or 25-OH-D$_2$, and hence underestimates the total concentration of circulating 25-OH-D.

In summary, 25-OH-D and 1,25(OH)$_2$D assays, known to date, suffer from various disadvantages, including long turn-around time, inter-assay variabilities, high cost and, in particular, the intrinsic use of radioactivity (in most assays), and are not best-suited for routine clinical assays. Furthermore, some of these assays (i.e., HPLC assay) require a fairly large volume of serum. This is a serious problem particularly in cases of neonates, infants and young children. Hence, there is an urgent need for a non-radioactive and highly sensitive method for assaying 25-OH-D and 1,25(OH)$_2$D in blood which will not be tedious, time-consuming and very expensive. The present invention overcomes these problems by providing a novel non-radioactive method for assaying 25-OH-D and 1,25 (OH)$_2$D in blood that is rapid, relatively inexpensive and easy to perform.

The measurement of 1,25(OH)$_2$D is very valuable in determining the etiology of inborn and acquired disorders of 25-OH-D metabolism (Holick (1989)). Therefore, the assay of 1,25(OH)$_2$D is valuable clinically and a new method that is rapid and does not use radioactivity is highly desirable.

A large number of active vitamin D compounds are known which are useful for various therapeutic purposes. See, for example, U.S. Pat. Nos. 5,457,217, 5,414,098, 5,384,313, 5,373,004, 5,371,249, 5,430,196, 5,260,290, 5,393,749, 5,395,830, 5,250,523, 5,247,104, 5,397,775, 5,194,431, 5,281,731, 5,254,538, 5,232,836, 5,185,150, 5,321,018, 5,086,191, 5,036,061, 5,030,772, 5,246,925, 4,973,584, 5,354,744, 4,927,815, 4,857,518, 4,851,401, 4,851,400, 4,847,012, 4,755,329, 4,940,700, 4,619,920, 4,594,192, 4,588,716, 4,564,474, 4,552,698, 4,588,528, 4,719,204, 4,719,205, 4,689,180, 4,505,906, 4,769,181, 4,502,991, 4,481,198, 4,448,726, 4,448,721, 4,428,946, 4,411,833, 4,367,177, 4,336,193, 4,360,472, 4,360,471, 4,307,231, 4,307,025, 4,358,406, 4,305,880, 4,279,826, and 4,248,791.

Vitamin D content in milk is determined by a laborious assay (Holick et al., *N. Eng. J. Med.* 132:1178–81 (1992), Tanner et al., *J. Assoc. of Analyt. Chem.* 17:607–710 (1988)). Thus, there is a need for a rapid non-radioactive assay for vitamin D in milk, blood, body fluids, foods and animal feed. These non-radioactive assays can be used to detect the presence of therapeutically useful vitamin D compounds.

SUMMARY OF THE INVENTION

The present invention relates to a compound having the formula:

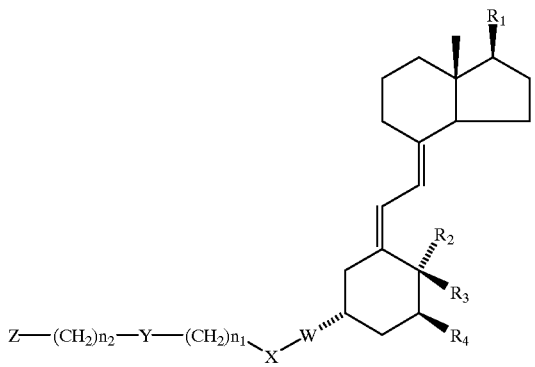

wherein:

R$_1$ is a substituted or unsubstituted alkyl, alkenyl or alkynyl group having 1 to 15 C-atoms which may be substituted by one or more hydroxy, halo, lower alkoxy, oxo, oxime, lower alkanoyloxy, aryloxy, aryl, benzoyl, a C$_4$ lactone, a C$_4$ lactone substituted by a methyl and a hydroxy group, C$_3$–C$_6$ cycloalkyl, or C$_3$–C$_6$ cycloalkyl substituted by hydroxy, lower alkyl, or hydroxyloweralkyl;

R$_2$ is a methyl group and R$_3$ is hydrogen, or
R$_2$ is hydrogen and R$_3$ is a methyl group, or
R$_2$ and R$_3$ are both hydrogen or,
R$_2$ and R$_3$ together are a methylene group (=CH$_2$),
R$_4$ is hydrogen, hydroxy, lower alkoxy or lower alkanoyloxy,
W is oxygen or amino;
X is carbonyl (C=O) or methylene (CH$_2$);
Y is oxygen, sulfur, amino —C(O)O— or —C(O)—NH—;
Z is biotin, a fluorescent group or a chemiluminescent group; and n$_1$ and n$_2$ are independently 1, 2, 3, 4, or 5.

The invention also relates to an assay method for the presence of vitamin D compounds in a sample, the improvement comprising using as the labeled vitamin D compound, a labeled compound of the present invention.

The invention also relates to a solid phase assay method for detecting a vitamin D, its metabolite or analog, comprising (a) providing a solid phase support having immobilized thereon a protein or antibody which is capable of binding to the labeled compound of the present invention;

(b) contacting said solid phase support with a solution of the labeled compound of the invention for a time sufficient to allow binding of the labeled compound to said protein or antibody;

(c) washing the solid phase support obtained in step (b) for a time sufficient to remove unbound labeled compound;

(d) contacting the solid phase support obtained in step (c) with a liquid sample suspected of obtaining a vitamin D, its metabolite or analog for a time sufficient to effect displacement of the labeled compound from said protein or antibody;

(e) removing the liquid obtained in step (d); and (f) detecting the presence of the labeled compound in the liquid obtained in step (e);

wherein the amount of labeled compound detected in step (f) is directly proportional to the amount of the vitamin D, its metabolite or analog in said test sample.

DETAILED DESCRIPTION OF THE PREFERRED EMBODIMENTS

Figure 1:
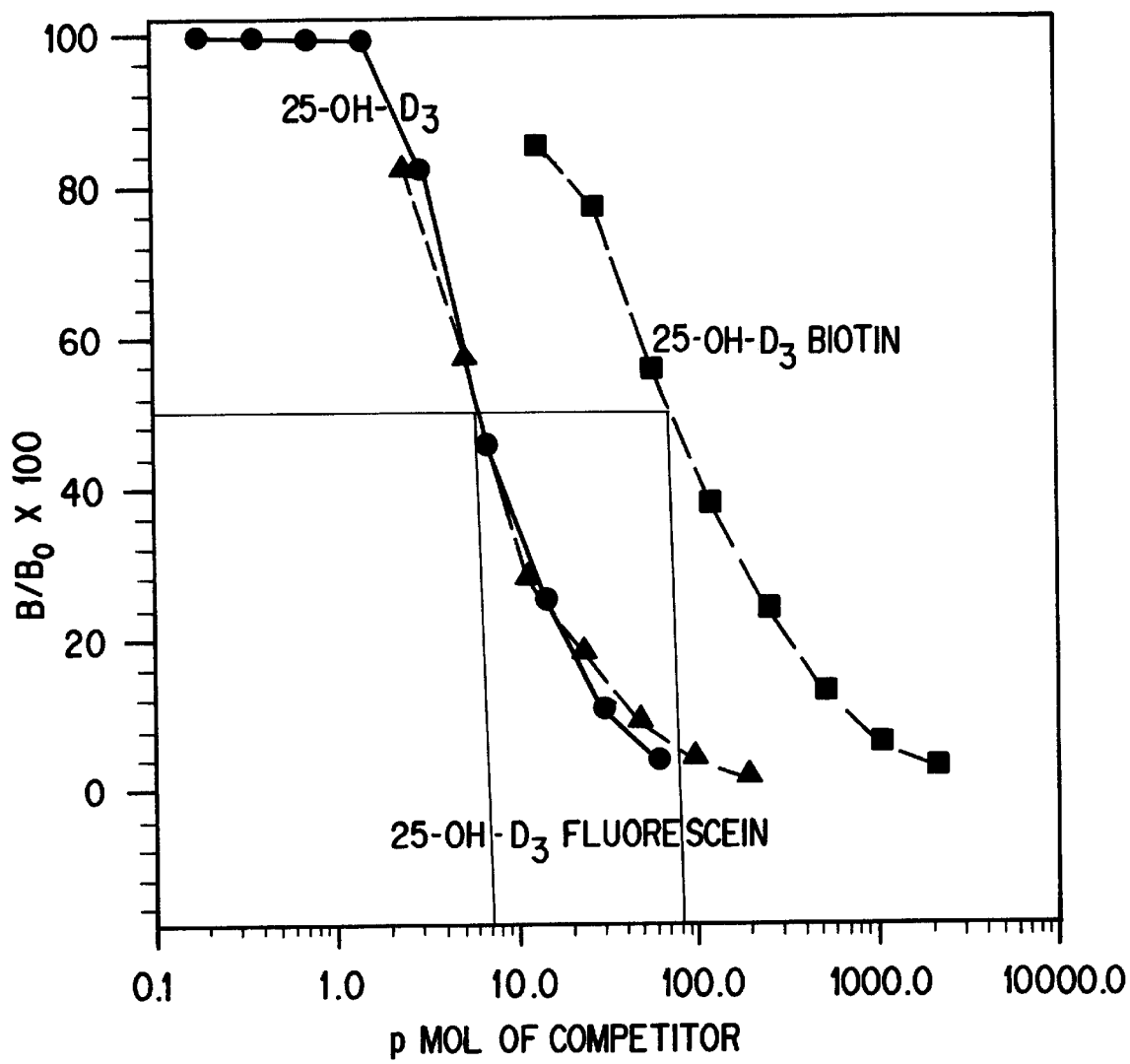
FIG. 1 depicts a competitive binding assay for 25-OH-$D_3$ biotin and fluorescein conjugates.
Figure 2:
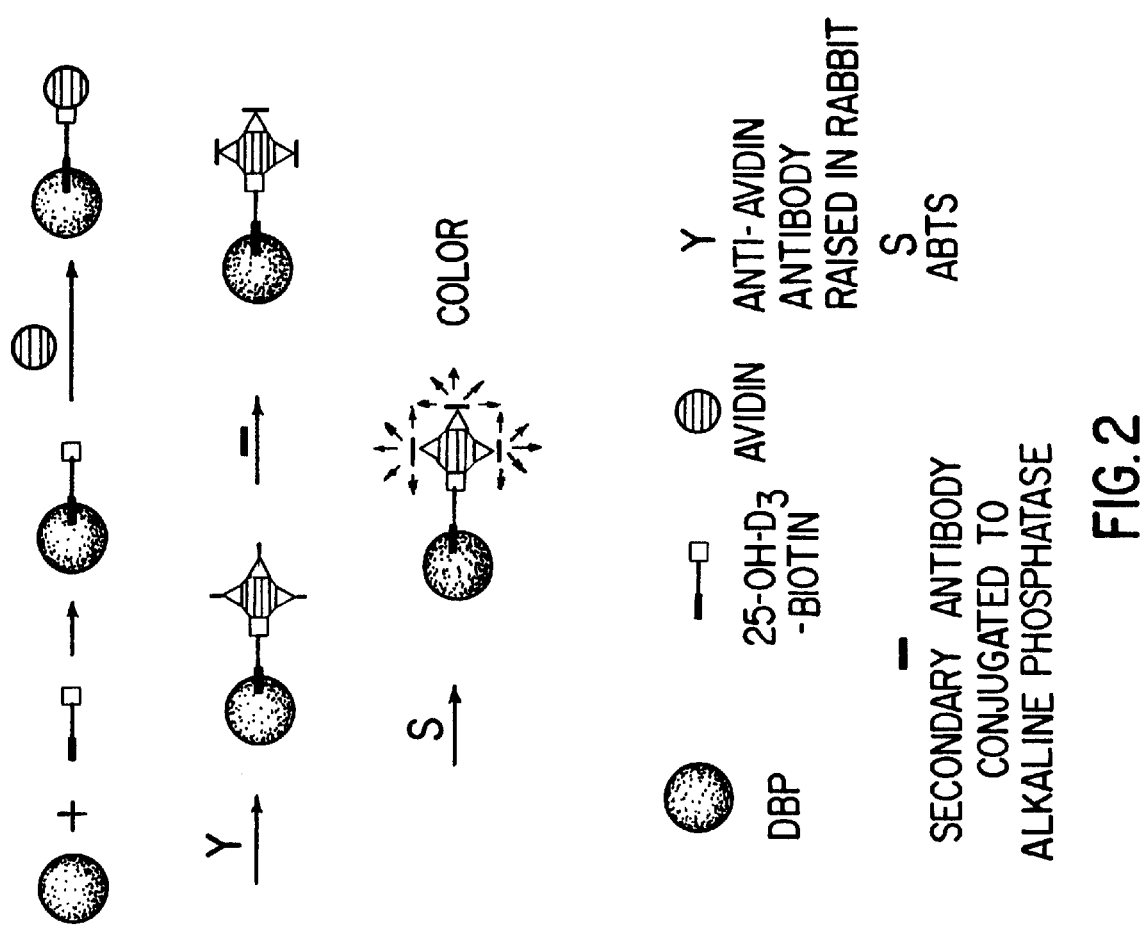
FIG. 2 depicts a schematic representation of the assay of the invention.
Figure 3:
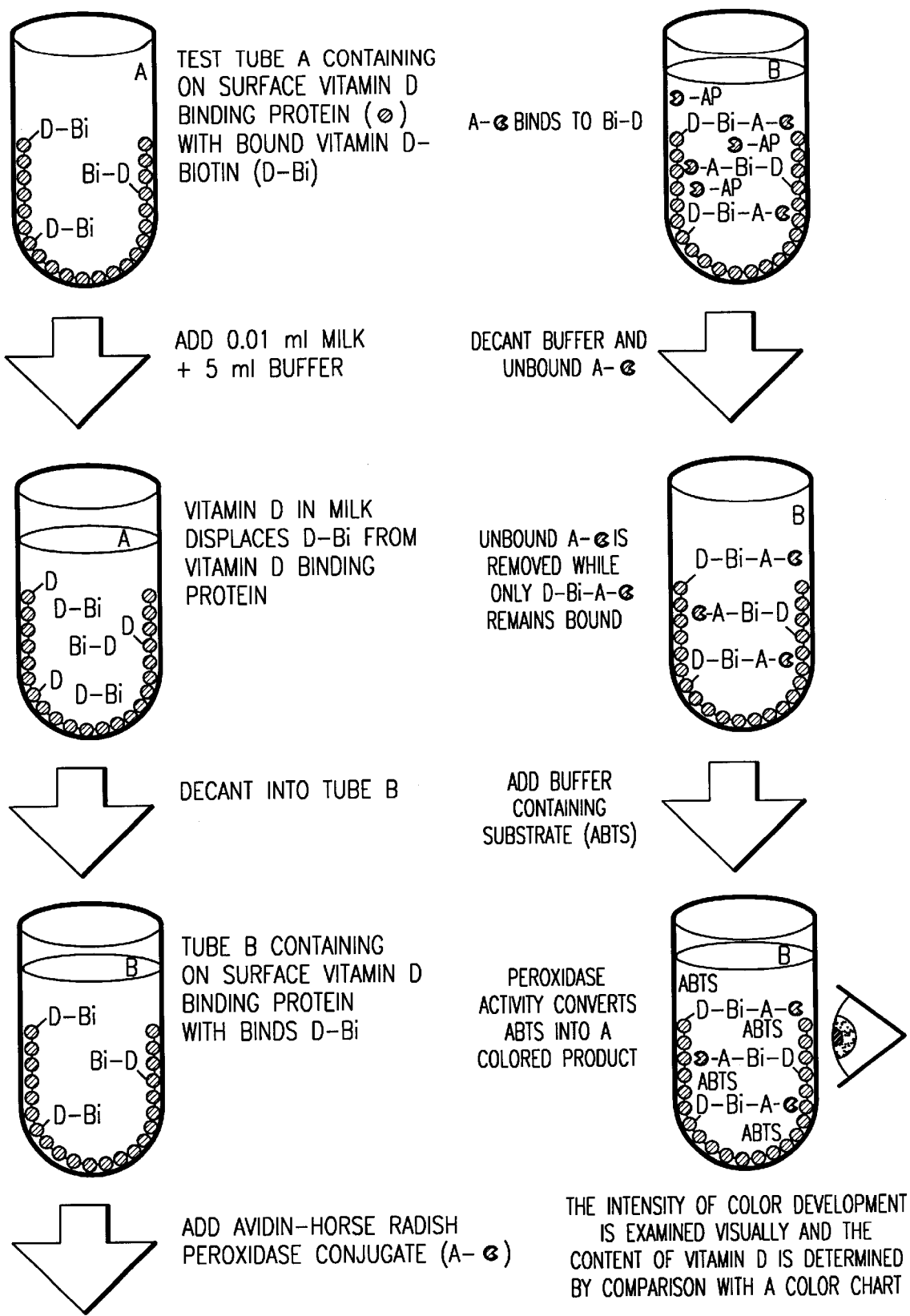
FIG. 3 depicts a vitamin D assay flow diagram for milk.

With respect to the formula above:

Typical $C_{6-14}$ aryl groups include phenyl, naphthyl, phenanthryl, anthracyl, indenyl, azulenyl, biphenyl, biphenylenyl and fluorenyl groups.

Typical halo groups include fluorine, chlorine, bromine and iodine.

Typical $C_{1-15}$ alkyl groups include methyl, ethyl, propyl, isopropyl, butyl, pentyl, hexyl, heptyl, octyl, nonyl, decyl groups as well as branched chain alkyl groups. Preferably, when $R_1$ is an alkyl group, it is the C-17 side chain of vitamin $D_2$ or $D_3$.

Typical $C_{2-15}$ alkenyl groups include ethenyl, propenyl, butenyl, pentenyl, hexenyl, heptenyl, octenyl, nonenyl, decenyl groups and the like as well as the branched chain alkenyl groups. Preferably, when $R_1$ is an alkenyl group, it is the C-17 side chain of vitamin $D_2$ or $D_3$ with a double bond at C22-23.

Typical $C_{2-4}$ alkynyl groups include ethynyl, propynyl, butynyl, pentynyl, hexynyl, heptynyl, octynyl, nonynyl, decynyl groups and the like as well as the branched chain alkynyl groups. Preferably, when $R_1$ is an alkynyl group, it is the C-17 side chain of vitamin $D_3$ with a triple bond at C22-23.

Typical lower alkoxy groups include oxygen substituted by one of the $C_{1-4}$ alkyl groups mentioned above.

Typical lower alkanoyloxy groups include any $C_{1-6}$ acyloxy groups, e.g. acetoxy, propanoyloxy, butanoyloxy, pentanoyloxy, hexanoyloxy and the like.

Typical aryloxy groups include oxygen substituted by any one of the aryl groups mentioned above.

Preferably, $R_1$ is a side chain of vitamin $D_2$ (carbon positions $C_{20}$–$C_{27}$) or $D_3$ (carbon positions $C_{20}$–$C_{27}$), or these chains partially modified with one or more hydroxy groups on $C_{23}$, $C_{24}$ and/or $C_{25}$.

Preferably, Z is biotin, fluorescein or any of their natural or synthetic derivatives or any other synthetic or natural derivatives which are ascribed to function as biotin or fluorescein (e.g., (4,4-difluoro-4-bora-3a,4a-diaza-5-indacene (BODIPY), rhodamine, phycoertherin, phycocyanin, allophycocyanin, o-phthaldehyde and fluorescamine). Z may also be a chemiluminescent molecule such as luminol, isoluminol, thermomatic acridium ester, imidazole, acridinium salt and 1,2-dioxetanes (see U.S. Pat. Nos. 4,931,569, 4,959,182, 5,004,565, 4,857,652, and 4,962,192).

The label may instead be attached at the 1-position of the vitamin D compound. In this embodiment, $R_4$ is the $C_3$ substituent depicted in the formula above, and there is a hydroxy group at the 3beta position.

Preferred labeled compounds include 25-hydroxy-3-aminopropoxyvitamin $D_3$ biotinamide, 25-hydroxy-3beta-[(5-biotinamidyl)pentanamido]-3-aminopropoxyvitamin $D_3$, 25-hydroxy-3beta-[(6-biotinamidyl)-hexanamido]-3-aminopropoxyvitamin $D_3$, 25-hydroxy-3beta-aminopropoxyvitamin $D_3$ fluorescein amide, 1,25-dihydroxy-3-aminopropoxyvitamin $D_3$ biotinamide, 1,25-dihydroxy-3beta-[(5-biotinamidyl)pentanamido]-3-aminopropoxyvitamin $D_3$, 1,25-dihydroxy-3beta-[(6-biotinamidyl)-hexanamido]-3-aminopropoxyvitamin $D_3$, 1,25-dihydroxy-3beta-aminopropoxyvitamin $D_3$ fluorescein amide, 3-aminopropoxyvitamin $D_3$ biotinamide, 3beta-[(5-biotinamidyl)pentanamido]-3-aminopropoxyvitamin $D_3$, 3beta-[(6-biotinamidyl)-hexanamido]-3-aminopropoxyvitamin $D_3$, and 3beta-aminopropoxyvitamin $D_3$ fluorescein amide.

The labeled compounds of the invention are ideally suited for the preparation of a kit. Such a kit may comprise a carrier means being compartmentalized to receive in close confinement therein one or more container means such as vials, tubes, plates and the like, each of the container means comprising the separate components of the assay. For example, there may be a container means containing the labeled vitamin D compound of the invention, optionally in solution or bound to the walls of the container. Further container means may contain, for example, avidin coated beads, plates or tubes; proteins which bind vitamin D compounds, their metabolites and/or analogs; DBP; enzyme labeled antibodies, vitamin D binding protein or vitamin D receptor and their substrates; and/or buffers such as phosphate buffer saline (PBS) or bovine serum albumin (BSA).

The labeled compounds of the present invention may be used in any conventional assay for vitamin D compound, their metabolites and for vitamin D analogs that may be administered to a patient. Such assays are competitive binding assays and enzyme linked immunoassays (ELISAs). See, for example, Chen et al., *J. Nutr. Biochem.* 1:272–276 (1990); Chen et al., *J. Nutr. Biochem.* 1:315–319 (1990); Chen et al., *J. Nutr. Biochem.* 1:320–327 (1990); Engvall, V. *Meth. Enzymol.* 70:419–439 (1980); Millipore Catalogue 1994–1995, Marlborough, Mass.; and U.S. Pat. Nos. 4,297,289, 4,816,417, 5,232,836 and 4,585,741. The improvement which comprises the present invention is the substitution of the labeled vitamin D compounds of the present invention for the prior art radiolabeled compounds.

The invention also relates to a solid phase assay method for detecting a vitamin D, its metabolite or analog in a test sample, comprising (a) providing a solid phase support having immobilized thereon a protein or antibody which is capable of binding to the labeled compound of the present invention;

(b) contacting said solid phase support with a solution of the labeled compound of the invention for a time sufficient to allow binding of the labeled compound to said protein or antibody;

(c) washing the solid phase support obtained in step (b) for a time sufficient to remove unbound labeled compound;

(d) contacting the solid phase support obtained in step (c) with a liquid test sample suspected of containing a vitamin D, its metabolite or analog for a time sufficient to effect displacement of the labeled compound from said protein or antibody;

(e) removing the liquid obtained in step (d); and (f) detecting the presence of the labeled compound in the liquid obtained in step (e);

wherein the amount of labeled compound detected in step (f) is directly proportional to the amount of the vitamin D, its metabolite or analog in said test sample.

Test samples which may be tested with the assay include extracts of animal feeds, foods containing vitamin D, milk, infant formula, blood, serum, urine, saliva, peritoneal and pleural fluids as well as pills or medicaments that contain vitamin D or its metabolites or analogs.

Examples of solid phase supports include glass, plastic, nitrocellulose, diazocellulose, polystyrene, polyvinylchloride, polypropylene, polyethylene, dextran, Sepharose, agar, starch, nylon and microtitre plates.

Proteins which bind to the labeled vitamin D compounds include any such protein which is known. Typically, such proteins are receptor proteins which bind vitamin D, its metabolites and/or analogs. Preferred proteins are vitamin D binding protein (DBP), vitamin D receptor or avidin.

Alternatively, any antibody which is capable of binding vitamin D, its metabolite or analog can be used.

The solid support may be washed with any conventional buffer such as PBS and the like.

The label can be detected by any means known, for example, by visual inspection, fluorometric or spectrophotometric means. Methods for detecting such labels in solid phase assays are disclosed in U.S. Pat. No. 5,098,846.

The labeled compounds of the present invention can be prepared according to the examples which follow. The starting vitamin D compounds and vitamin D analogs can be obtained according to the methods disclosed in U.S. Pat. Nos. 5,457,217, 5,414,098, 5,384,313, 5,373,004, 5,371, 249, 5,430,196, 5,260,290, 5,393,749, 5, 5,321,018, 5,086, 191, 5,036,061, 5,030,772, 5,246,925, 4,973,584, 5,354,744, 4,927,815, 4,857,518, 4,851,401, 4,851,400, 4,847,012, 4,755,329, 4,940,700, 4,619,920, 4,594,192, 4,588,716, 4,564,474, 4,552,698, 4,588,528, 4,719,204, 4,719,205, 4,689,180, 4,505,906, 4,769,181, 4,502,991, 4,481,198, 4,448,726, 4,448,721, 4,428,946, 4,411,833, 4,367,177, 4,336,193, 4,360,472, 4,360,471, 4,307,231, 4,307,025, 4,358,406, 4,305,880, 4,279,826, and 4,248,791.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLES

Example 1

Biotin Conjugate of Vitamin $D_3$-3-Amino Propyl Ether (A)

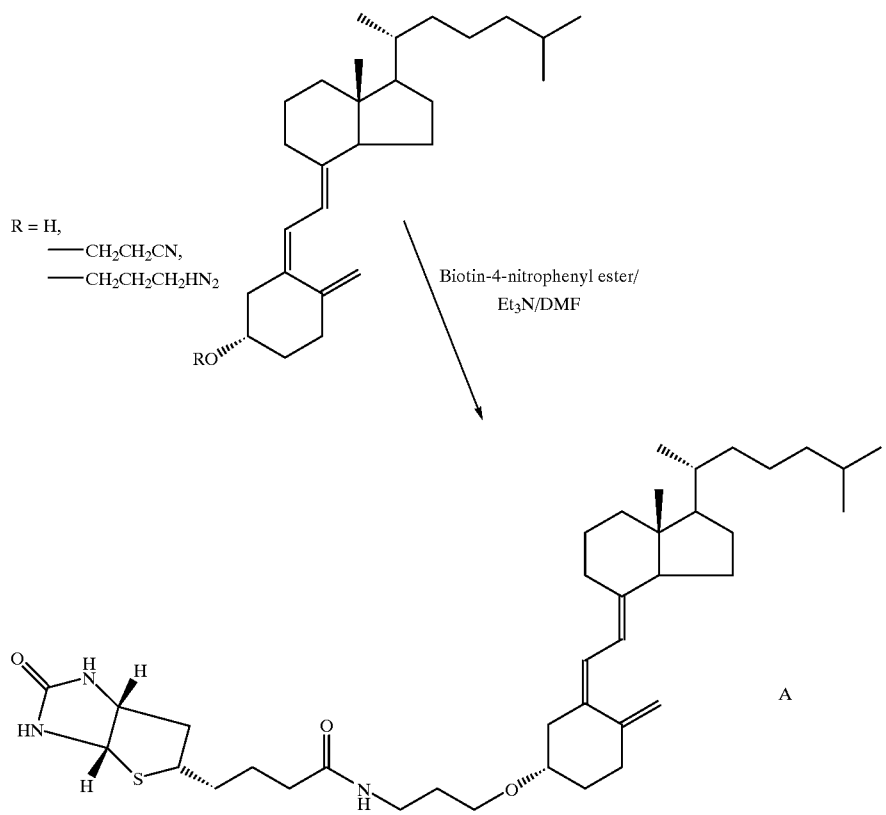

Compound A was synthesized by the reaction of vitamin $D_3$-3-aminopropyl ether with biotin-4-nitrophenyl ester in dimethyl formamide (DMP) in the presence of triethylamine ($Et_3N$). The product was purified by preparative TLC. Yield of A was 70%. NMR spectrum of A supported its structure. Related compounds of the invention may be prepared by reaction of the corresponding vitamin $D_3$-aminopropyl ether.

Example 2

Biotin Conjugate of 25-Hydroxyvitamin $D_3$-3-Aminopropyl Ether (B)

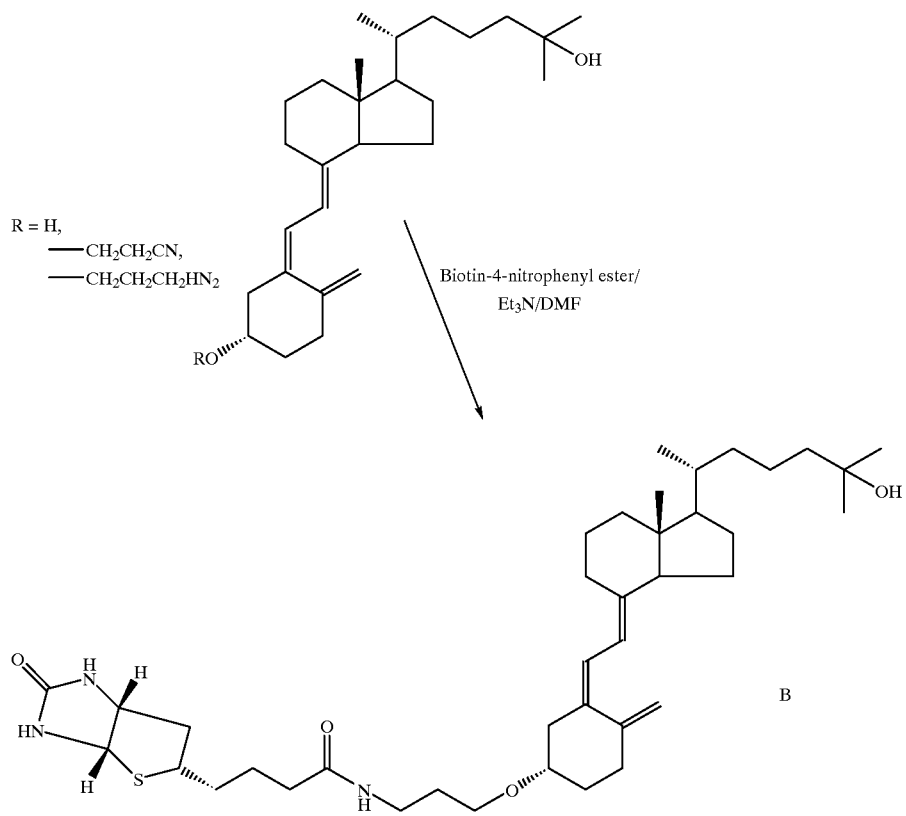

Compound B was synthesized by the reaction of 25-OH-$D_3$-3-aminopropyl ether with biotin-4-nitrophenyl ester (Aldrich Chemical Co.) in DMF in the presence of $Et_3N$. The product was purified by the preparative TLC on silica gel (10% methanol in methylene chloride) in 45% yield. The adduct B had a UV spectrum having $\lambda_{max}$ at 265 nm. Spectrum of B was confirmed by NMR.

Example 3

Conjugate of 25-OH-D$_3$-3-Aminopropyl Ether and Biotin-X-NHS (C)

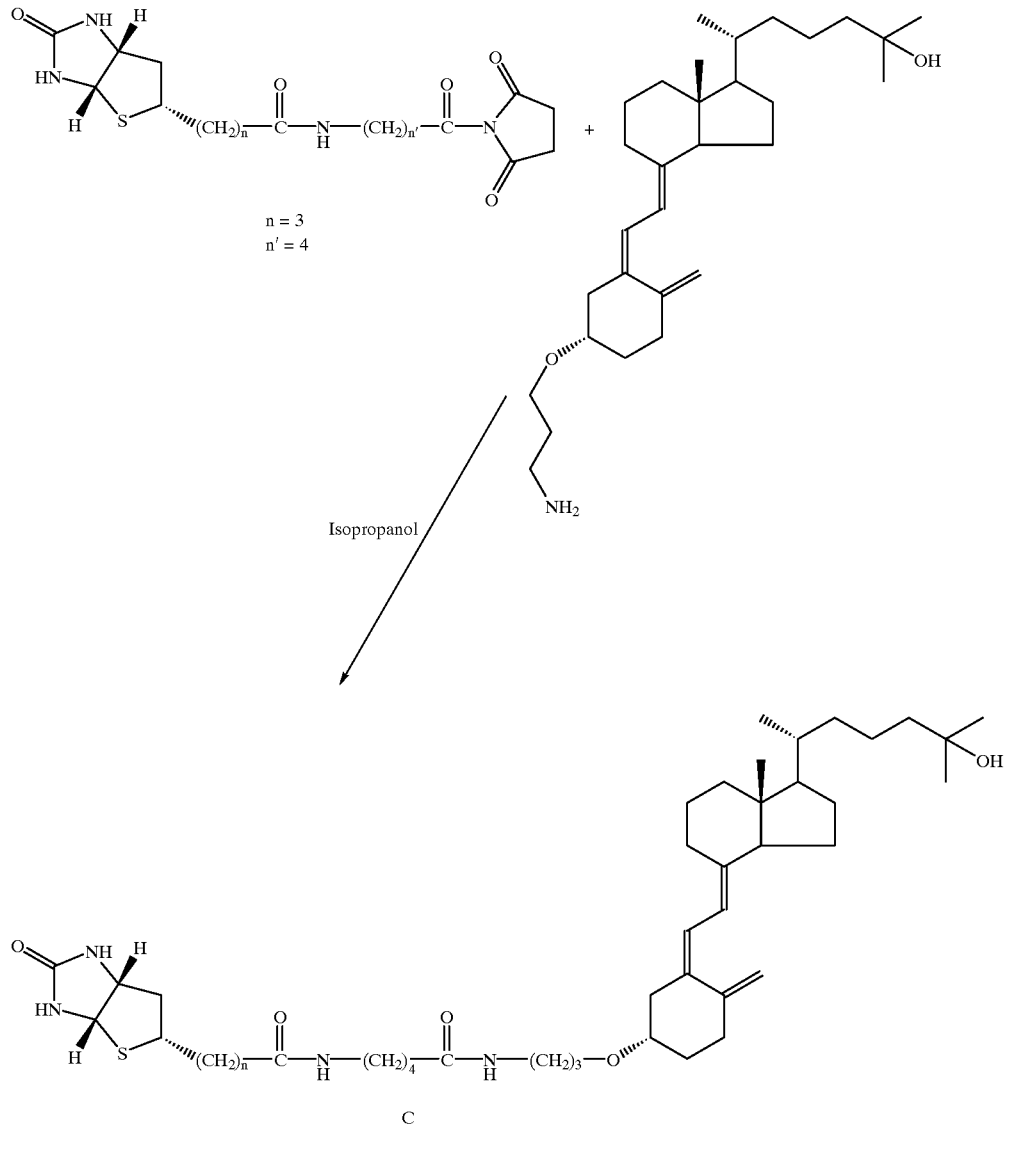

The solution of 25-OH-D$_3$-aminopropyl ether and biotin-X-NHS (Calbiochem Inc., San Diego Calif.) in isopropanol was stirred for one hour followed by the addition of a small amount of n-butylamine for dissipating the unreacted biotin-X-NHS. After an hour of stirring the solution was dried under argon and the reaction mixture was purified by preparative TLC (10% methanol in CH$_2$Cl$_2$). There were primarily two UV-active bonds. The polar band was further purified by HPLC (C$_{18}$ column, 5% water in MeOH). UV spectrum of compound C in methanol had a vitamin D-like spectrum with $\lambda_{max}$ at 265 nm and a $\lambda_{min}$ at 228 nm. NMR spectrum of C was consistent with its structure.

Example 4

Synthesis of a Conjugate of 25-OH-$D_3$-3-Aminopropyl Ether and a Fluorescein Derivative (F)

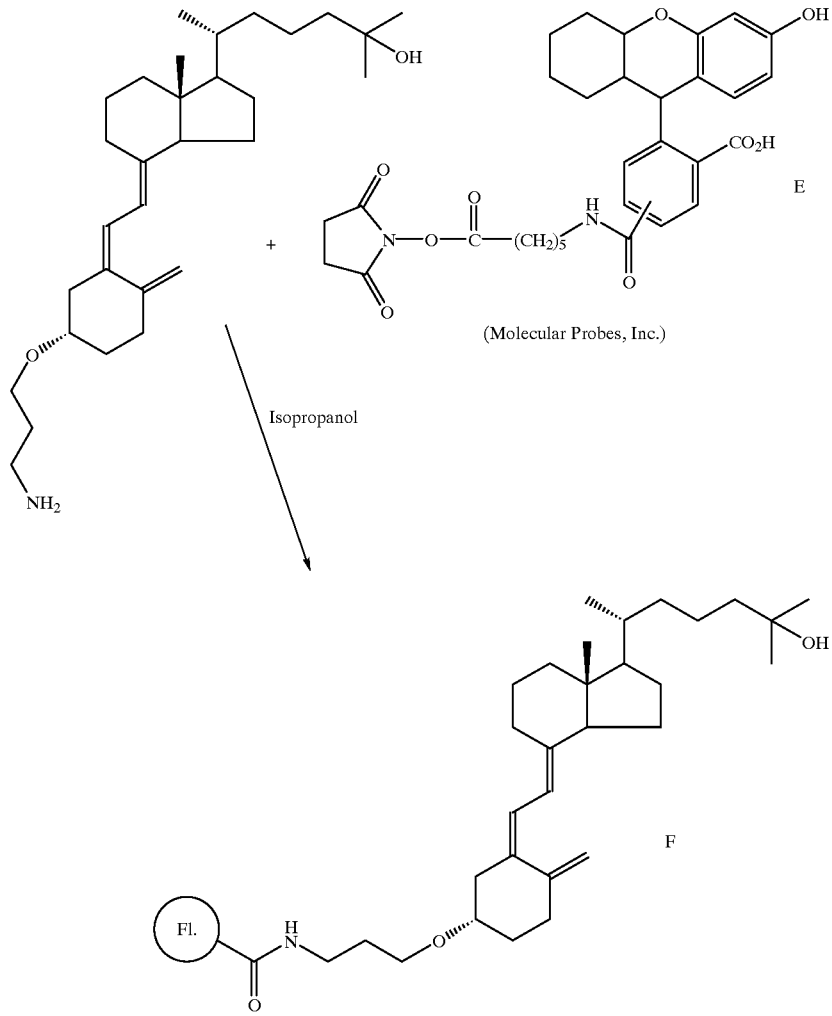

(Molecular Probes, Inc.)

A solution of fluorescein compound E (6-(fluorescein-5-(and 6-)-carboxamidohexanonic acid succinyl ester, Molecular Probes, Inc., Eugene, Oreg.) and an excess of the 25-OH-$D_3$-3-aminopropyl ether in isopropanol was stirred for an hour followed by the removal of solvent. TLC of this reaction mixture (acetic acid:acetone:methanol:benzene—0.25:0.25:0.25:0.5:4.0) indicated the formation of a strongly fluorescent compound. It was isolated by preparative TLC using the same eluant.

Example 5

Biotin Conjugate of 25-OH-$D_3$-3-Aminopropyl-3-(6-Amino) Hexanoic Acid (D)

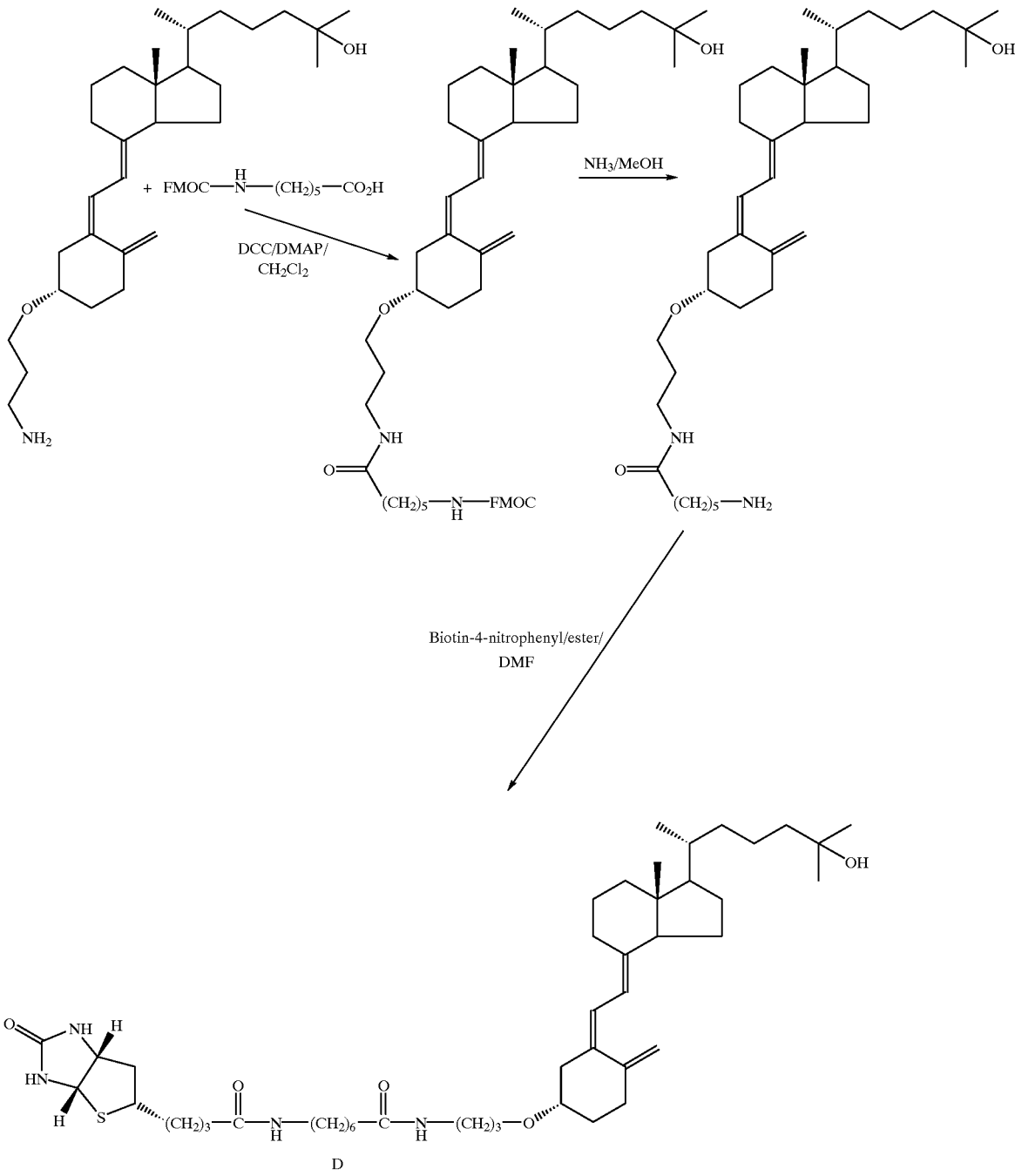

The compound D was synthesized according to this scheme. The product was characterized by UV (methanol), which had a $\lambda_{max}$ of 265 mm, typical for vitamin D-triene system. NMR spectrum of D: δ4.8 and 5.1 ($AB_q$ pattern, exocyclic $CH_2$, 2H), δ5.9 and 6.2 (double doublet, 2H, $CH_2$ olefinic proton).

Example 6

Competitive Radioligand Binding Assays of Analogs (C) and (F) with Human Vitamin D-Binding Protein (hDBP)

These assays were carried out to determine the viability of these synthetic analogs to serve as substrates for hDBP. It was observed that, on a molar basis, compound C was approximately eleven (11) times less efficient in displacing $^3$H-25-OH-$D_3$, bound to hDBP, than 25-OH-$D_3$. Compound F was similar to 25-OH-$D_3$ in displacing $^3$H-25-OH-$D_3$ (FIG. 1). The results shown in FIG. 1 demonstrate that compound C and D can replace 25-OH-$D_3$ for DBP binding.

Example 7

Development of an Enzyme-Linked Immunosorption Assay (ELISA) for Measuring the Concentration of Vitamin $D_3$ and 25-OH-$D_3$ in a Test Solution The method involves attachment of DBP to an ELISA plate followed by the addition of a known quantity of 25-OH-$D_3$-biotin conjugate (compound C). This compound gets bound to DBP (attached to the plate) due to strong binding affinity between DBP and 25-OH-$D_3$. Excess amount of C is washed off, and an excess of avidin is added which gets bound to biotin attached to 25-OH-$D_3$. The plate is then incubated in sequence with anti-avidin antibody, a secondary antibody coupled to horseradish peroxidase (HRP), and ABTS (2,2'-azino-di-(3-ethylbenzthiazoline) sulfonate, the substrate that produces a blue color which may be monitored spectrophotometrically or visually. The intensity (absorbance) of the color is directly proportional to the concentration of compound C. In the first experiment, the optimal concentrations of DBP and compound C to develop color were determined (visually). In this experiment, each sample of DBP was tested against each amount of compound C.

A. Determination of the optimal amount of DBP and compound (C) in a checkerboard titration (ELISA) to obtain a colorimetric signal DBP used: 200, 100, 50, 25, 12.5, 6.25, 3.125 ng
C used: 1, 0.5, 0.25, 0.125, 0.066, 0.033, 0.016 $\mu$g Flowchart Add different amounts of purified hDBP (From Calbiochem, San Diego, Calif., in 100 mM $Na_2CO_3$ buffer, pH 8.4) to wells of an ELISA plate
↓ Incubate at 37° C.
Block excess sites with BSA (1 mg/ml, 300 $\mu$l)
↓ wash with PBS containing 0.05% TWEEN 20
Add different amounts of C in EtOH
↓ Incubate at 4° C.
Wash with PBS containing 0.05% TWEEN 20 (Biorad, Richmond, Calif.)
↓
Add 100 ng of avidin (Sigma Chemical Co., St. Louis, Mo.) in 100 mM $NaCO_3$, pH 8.4
↓ Incubate at 4° C.
Wash with PBS buffer, then add primary anti-avidin antibody (Sigma Chemical Co., St. Louis, Mo.)
↓ Incubate at 4° C.
↓ Wash with PBS and TWEEN 20
Add secondary antibody (anti-rabbit IgG from donkey, Amersham Corp., Springfield, Ill.) coupled to HRP
| Incubate at 4° C.
↓ Wash with PBS and TWEEN 20
Add substrate (ABTS; 2,2'-azino-di-(3-ethylbenzathiazoline)sulfonate)
↓ Incubate at 25° C.
Color development detected visually or spectrophotometrically.
Results: minimum amounts of DBP and compounds (C) required to obtain yellow color were 6.25 ng and 30 ng, respectively.

In the next experiment, it was determined whether it would be possible to displace compound C, bound to DBP (which is attached to an ELISA plate), with a known concentration of 25-OH-$D_3$. In a real sample, one will be measuring the amount of 25-OH-D and not that of compound C.

B. Assays to demonstrate that compound C can be competed out with 25-OH-$D_3$

Three concentrations of DBP/C were chosen.

|   | DBP/C | 25-OH-$D_3$ |
|---|---|---|
| 1 | 6.25 ng/30 ng | 2 $\mu$g |
| 2 | 12.5 ng/60 ng | 2 $\mu$g |
| 3 | 25 ng/120 ng | 2 $\mu$g |

Procedure: same as before, except either C, or C and 2 $\mu$g of 25-OH-$D_3$ were added to each plate. Each concentration (point) was done in triplicate. The blank contained no 25-OH-$D_3$ or C.

Color was absent with all the samples containing 25-OH-$D_3$ demonstrating that 25-OH-$D_3$ is capable of displacing compound C bound to DBP on an ELISA plate. Furthermore, the amount of compound C is directly proportional to the concentration of added 25-OH-$D_3$. Hence, the amount of displaced compound C can be used as a measure of 25-OH-$D_3$ in the assay system.

An alternate method to measure vitamin D or 25-OH-D with high sensitivity is as follows.

Flowchart

1. Coat the wells of a micro-titer plate with 200 ng of DBP, 2 hours at 37° C.
2. Block excess sites with BSA (mg/ml in PBS-TWEEN 20 buffer), 2 hrs at 37° C.
3. Make a serial dilution of 25-OH-$D_3$ (36 pg to 8.76 ng) or vitamin $D_3$ (0.36 ng to 85 ng)
4. Add compound C (25-OH-$D_3$-biotin) (800 pg) either alone or with different concentrations of 25-OH-$D_3$ or vitamin $D_3$
5. Incubate at 4° C. for 12 hours
6. Wash the plate and incubate with avidin (100 ng/well) for 2 hrs at 4° C.
7. Wash the plate and incubate with antiavidin antibody (1:10,000 dilution) for 2 hrs at 4° C.
8. Wash the plate and incubate with HRP-coupled secondary antibody (1:5,000 dilution) for 2 hrs at 4° C.
9. Wash the plate and incubate with ABTS solution
10. Stop the reaction by adding 0.05 ml of 20% SDS solution
11. Read the OD of each well at 410 nm.

Figure 4:
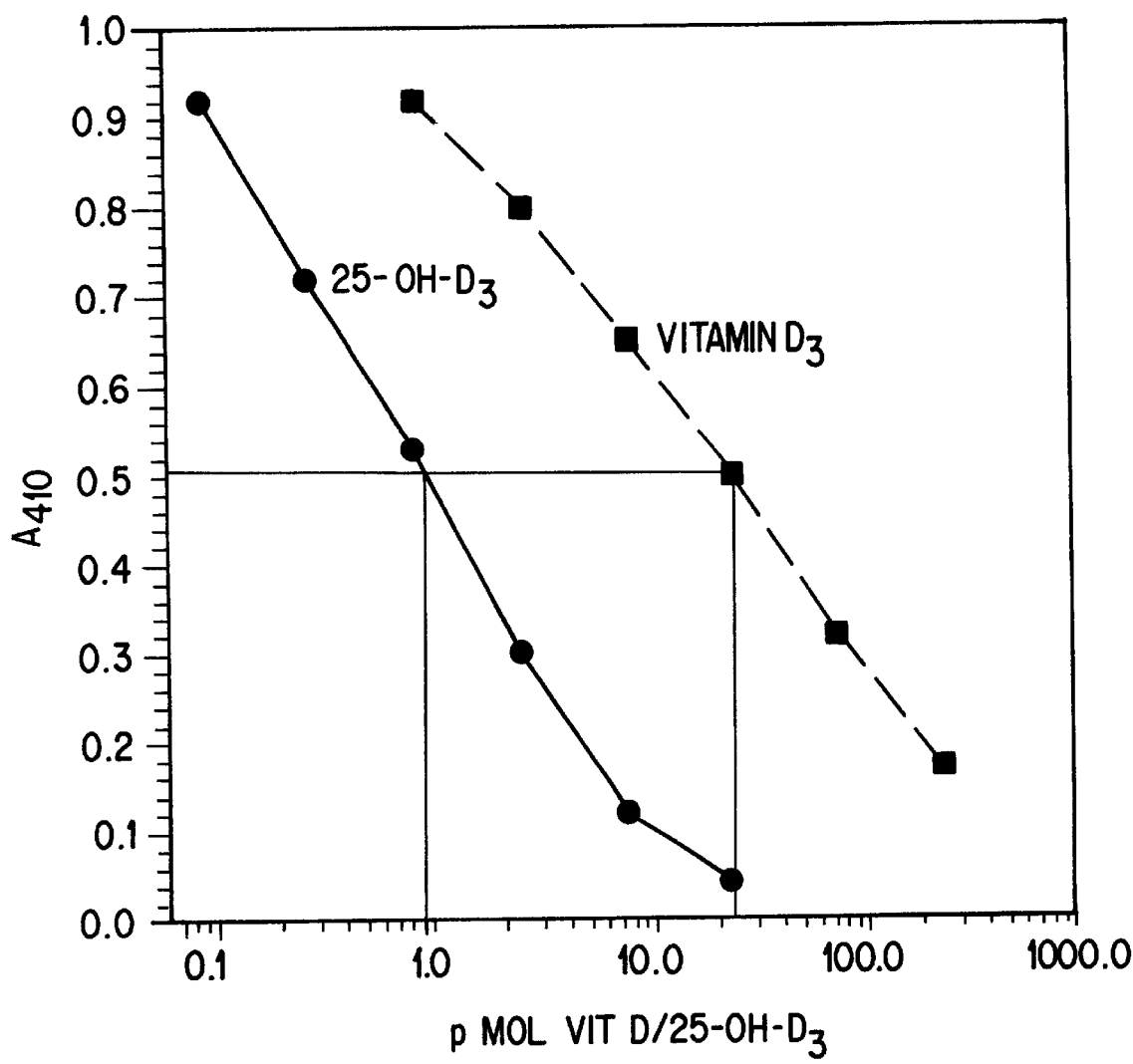
FIG. 4 depicts assays for vitamin $D_3$ and 25-OH-$D_3$ using the double-antibody technique.

Using the above procedure vitamin $D_3$ and 25-OH-$D_3$ were detected in picomolar levels as shown in FIG. 4.

Example 8

Assays for Vitamin $D_3$, 25-OH-$D_3$ and 1,25(OH)$_2D_3$ Using Avidin-Biotin Chemistry Stepwise procedure for an alternative method to measure vitamin $D_3$, 25-OH-$D_3$ and 1,25(OH)$_2D_3$ using biotin labeled vitamin D compounds is elaborated in the following.

Flowchart

1. Coat wells of a micro-titer plate with avidin (200 ng per well) in 100 mM sodium bicarbonate buffer, pH 8.4
2. Block excess sites with BSA (1 mg/ml in PBS containing 0.05% TWEEN 20) for 2 hrs at 37° C. Wash the wells 3. Couple DBP with horseradish peroxidase (DBP*) by standard protocol
4. Incubate DBP* (100 ng) with compound C (400 pg) in the presence and absence of different concentrations of vitamin $D_3$ (1.25, 2.5, 5.0, 10.0, 20.0, 40.0, 80.0, 160.0, 320.0, and 640 ng) or 25-OH-$D_3$ (20.0, 40.0, 80.0, 160.0, 320.0, 640.0, and 1280.0 pg) or 1,25$(OH)_2D_3$ (1.25, 2.5, 5.0, 10.0, 20.0, 40.0, 80.0, 160.0, 320.0, and 640 ng) in 50 mM Tris.HCl buffer, pH 8.3, 150 mM NaCl, 1.5 mM EDTA, 0.1% Triton X 100, in 1.5 ml microfuge tubes (total volume 0.1 ml) at 4° C. overnight
5. Add DBP*&/vitamin $D_3$ or DBP*/25-OH-$D_3$ or DBP*/1,25$(OH)_2D_3$ incubation mixtures to respective wells, allow to sit at 25° C. for 60 minutes
6. Wash the wells
7. Add substrate (ABTS) to each well, wait till color develops (10–20 minutes)
8. Stop the reaction by adding 0.05 ml of 20% SDS
9. Read OD at 410 nm.

Figure 5:
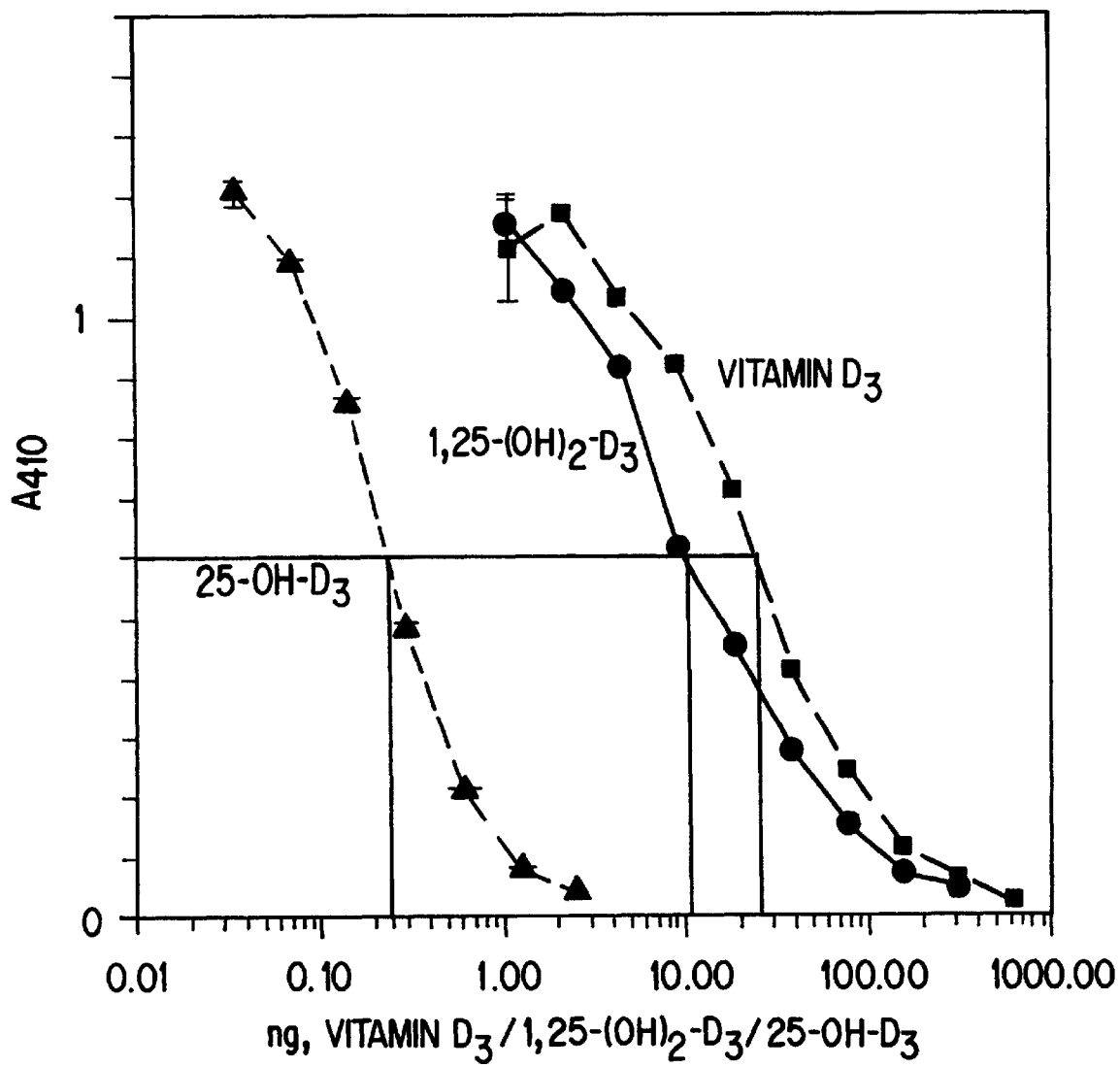
FIG. 5 depicts assays for vitamin $D_3$ and 25-OH-$D_3$ using the avidin-biotin chemistry technique.

Results of the above assay using standard samples of vitamin $D_3$, 25-OH-$D_3$ and 1,25$(OH)_2D_3$ are shown in FIG. 5.

Example 9

Synthesis of a Biotin Conjugate of 1,25(OH—$)_2D_3$ (1α,25-dihydroxyvitamin $D_3$-3β-(6-amidobiotinyl) hexanoate, G)

Assays for 1,25$(OH)_2D$ a biotin conjugate of 1,25$(OH)_2D_3$ which binds to vitamin D receptor (VDR) are also desirable. A biotinylated derivative of 1,25$(OH)_2D_3$ was prepared as follows.

Figure 6:
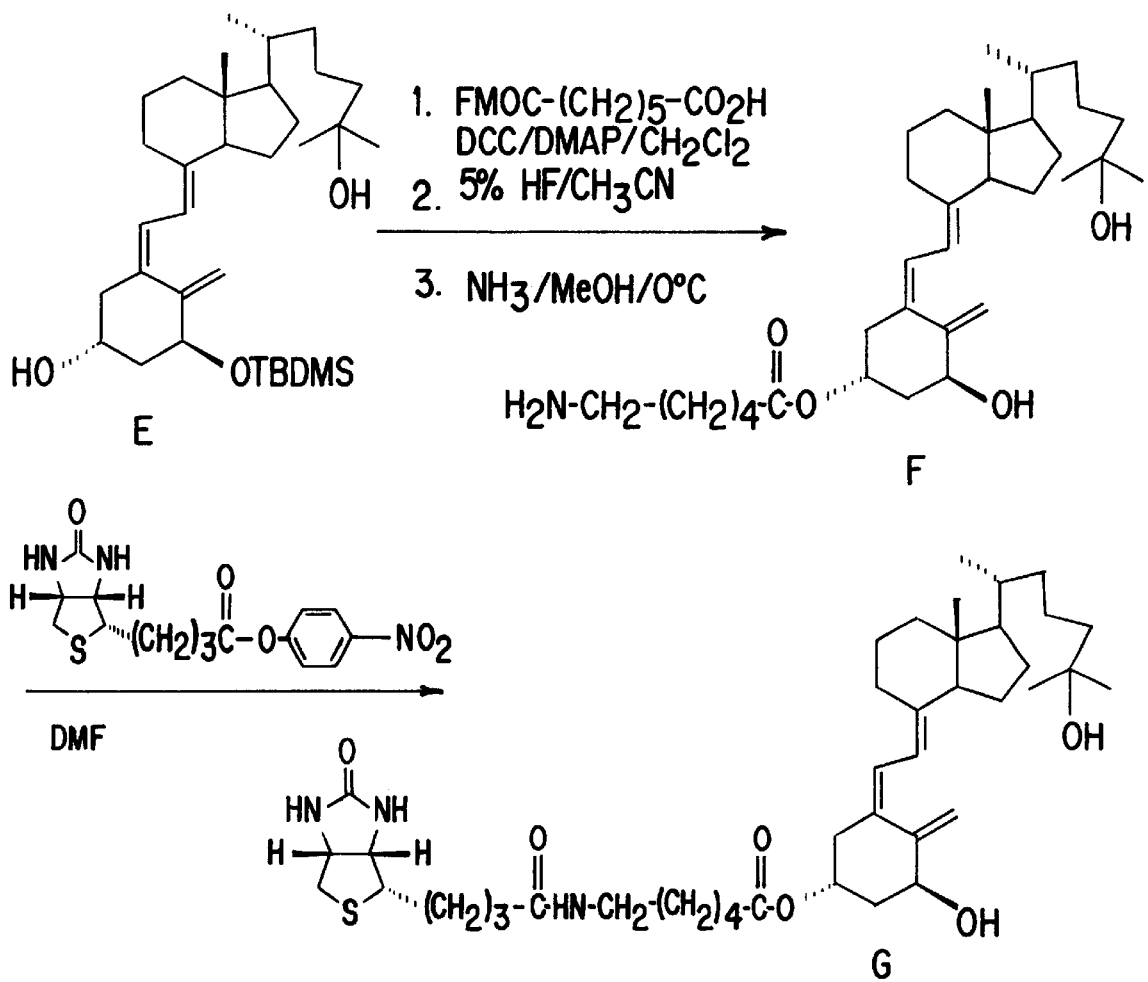
FIG. 6 depicts a scheme for the preparation of a biotin conjugate of 1,25($OH_2$)$D_3$.

The title compound (G) was synthesized in a multi-step procedure (FIG. 6) starting with a derivative of 1,25$(OH)_2D_3$ in which the 1α-OH group is protected as a tert. butyldimethylsilyl ether (TBDMS) (E) (Ray et al., *J. Chem. Soc.*, 702–703 (1985), Ray et al., *Biochem. Biophys. Res. Comm.* 132:198–203 (1985), Ray and Holick, *Steroids* 51: 623–630 (1988), Ray et al., *Steroids* 58: 462–465 (1993), Ray et al., *Bioorganic Chem.* 22: 276–283 (1994), Ray et al., *J. Biol. Chem.* 271: 2012–2017 (1996). DCC-coupling of compound E with FMOC-caproic acid, followed by the removal of the 1-OH— and FMOC-protecting groups produced the amine (F). Coupling of compound F with p-nitrophenyl ester of biotin produced the desired biotin conjugate of 1,25$(OH)_2D_3$ (compound G) in which biotin is attached to 1,25$(OH)_2D_3$ via a long tether. All the synthetic compounds were characterized by NMR and UV spectrometry.

From the foregoing description, one skilled in the art can easily ascertain the essential characteristics of this invention, and without departing from the spirit and scope thereof, can make various changes and modifications of the invention to adapt it to various usages and conditions without undue experimentation. All patents and publications cited herein are incorporated by reference in their entirety.

What is claimed is:

1. A kit comprising a carrier means having in close confinement therein one or more container means, wherein one container means contains the compound of formula:

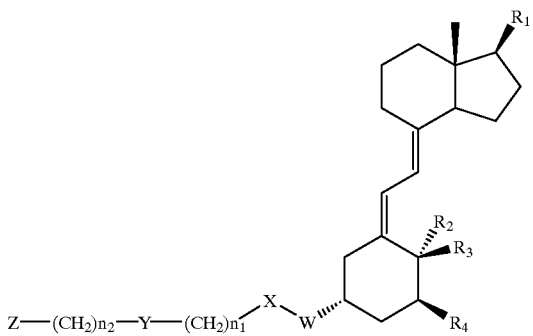

wherein:

$R_1$ is a substituted or unsubstituted alkyl, alkenyl or alkynyl group having 1 to 15 C-atoms which may be substituted by one or more halo, hydroxy, lower alkoxy, oxo, oxime, lower alkanoyloxy, aryloxy, aryl, benzoyl, a $C_4$ lactone, a $C_4$ lactone substituted by a methyl and a hydroxy group, $C_3$–$C_6$ cycloalkyl, or $C_3$–$C_6$ cycloalkyl substituted by hydroxy, lower alkyl, or hydroxyloweralkyl;

$R_2$ is a methyl group and $R_3$ is hydrogen, or $R_2$ is hydrogen and $R_3$ is a methyl group, or $R_2$ and $R_3$ are both hydrogen or, $R_2$ and $R_3$ together are a methylene group (=$CH_2$), $R_4$ is hydrogen, hydroxy, lower alkoxy or lower alkanoyloxy, W is oxygen or amino;

X is carbonyl (C=O) or methylene ($CH_2$);

Y is oxygen, sulfur, amino, —C(O)O— or —C(O)NH—;

Z is biotin, a fluorescent group or a chemiluminescent group; and $n_1$ and $n_2$ are independently 1, 2, 3, 4, or 5.

2. The kit of claim 1, wherein Z is biotin.

3. The kit of claim 1, wherein the compound is 25-hydroxy-3-aminopropoxyvitamin $D_3$ biotinamide.

4. The kit of claim 1, wherein the compound is 25-hydroxy-3beta-[(5-biotinamidyl)pentanamido]-3-aminopropoxyvitamin $D_3$.

5. The kit of claim 1, wherein the compound is 25-hydroxy-3beta-[(6-biotinamidyl)-hexanamido]-3-aminopropoxyvitamin $D_3$.

6. The kit of claim 1, wherein Z is a fluorescent group.

7. The kit of claim 1, wherein the compound is 25-hydroxy-3beta-aminopropoxyvitamin $D_3$ fluorescein amide.

8. The kit of claim 1, wherein the compound is 1,25-dihydroxy-3-aminopropoxyvitamin $D_3$ biotinamide.

9. The kit of claim 1, wherein the compound is 1,25-dihydroxy-3beta-[(5-biotinamidyl)pentanamido]-3-aminopropoxyvitamin $D_3$.

10. The kit of claim 1, wherein the compound is 1,25-dihydroxy-3beta-[(6-biotinamidyl)hexanamido]-3-aminopropoxyvitamin $D_3$.

11. The kit of claim 1, wherein the compound is 1,25-dihydroxy-3beta-aminopropoxyvitamin $D_3$ fluorescein amide.

12. The kit of claim 1, wherein the compound is 3-aminopropoxyvitamin $D_3$ biotinamide.

13. The kit of claim 1, wherein the compound is 3beta-[(5-biotinamidyl)pentanamido]-3-aminopropoxyvitamin $D_3$.

14. The kit of claim 1, wherein the compound is 3beta-[(6-biotinamidyl)hexanamido]-3-aminopropoxyvitamin $D_3$.

15. The kit of claim 1, wherein the compound is 3beta-aminopropoxyvitamin $D_3$ fluorescein amide.

16. The kit of claim 1, wherein $R_1$ is the side chain of vitamin $D_2$ or vitamin $D_3$.

17. The kit of claim 1, wherein $R_1$ is the side chain of vitamin $D_2$ or vitamin $D_3$ substituted with at least one hydroxy group at the $C_{23}$, $C_{24}$ or $C_{25}$ positions.

* * * * *